United States Patent [19]
Raskin et al.

[11] Patent Number: 6,010,501
[45] Date of Patent: Jan. 4, 2000

[54] METHOD AND APPARATUS FOR EXTERNAL FIXATION OF SMALL BONES

[75] Inventors: Keith B. Raskin, New York, N.Y.; Stephen B. Walulik, Phillipsburg; Kirk J. Bailey, Andover, both of N.J.

[73] Assignee: Electro-Biology, Inc., Parsippany, N.J.

[21] Appl. No.: 08/990,602

[22] Filed: Dec. 15, 1997

[51] Int. Cl.<sup>7</sup> ............................................ A61B 17/60
[52] U.S. Cl. ............................................ 606/54; 606/59
[58] Field of Search ............................ 606/54, 55, 56, 606/57, 58, 59

[56] References Cited

U.S. PATENT DOCUMENTS

| | | | |
|---|---|---|---|
| 4,548,199 | 10/1985 | Agee | 128/92 |
| 4,554,915 | 11/1985 | Brumfield | 128/92 |
| 4,611,586 | 9/1986 | Agee et al. | 128/92 |
| 4,628,919 | 12/1986 | Clyburn | 128/92 |
| 4,922,896 | 5/1990 | Agee et al. | 606/54 |
| 5,041,112 | 8/1991 | Mingozzi et al. | 606/54 |
| 5,391,167 | 2/1995 | Pong et al. | 606/57 |
| 5,405,347 | 4/1995 | Lee et al. | 606/54 |
| 5,437,666 | 8/1995 | Tepic et al. | 606/55 |
| 5,620,442 | 4/1997 | Bailey et al. | 606/54 |
| 5,662,650 | 9/1997 | Bailey et al. | 606/59 |

OTHER PUBLICATIONS

Agee, M.D., John M. and King, Francis C., Agee–WristJack Fracture Reduction System (Surgeon's Manual), undated, pp. 1–40.

*Primary Examiner*—Michael Buiz
*Assistant Examiner*—David O. Reip
*Attorney, Agent, or Firm*—Harness, Dickey & Pierce, P.L.C.

[57] ABSTRACT

An external fixator for securing a first bone portion in a fixed relationship with respect to a second bone portion. The fixator includes a bone screw clamping assembly for receiving a first bone screw which is connected to the first bone portion and which includes a spherical portion. The fixator further includes a bone screw clamping assembly which is operable to receive a second bone screw which is connected to the second bone portion and which has a spherical portion. The fixator also includes a connection member having a main body portion and an internal module adjustably mounted within the main body portion. The internal module receives a spherical end of one of the bone screw clamps and selectively permits universal movement thereof. The internal module may be linearly adjusted within the connection member independently in first and second directions which are substantially perpendicular to one another. The fixator further includes a locking mechanism for preventing universal movement of the spherical portion.

18 Claims, 3 Drawing Sheets

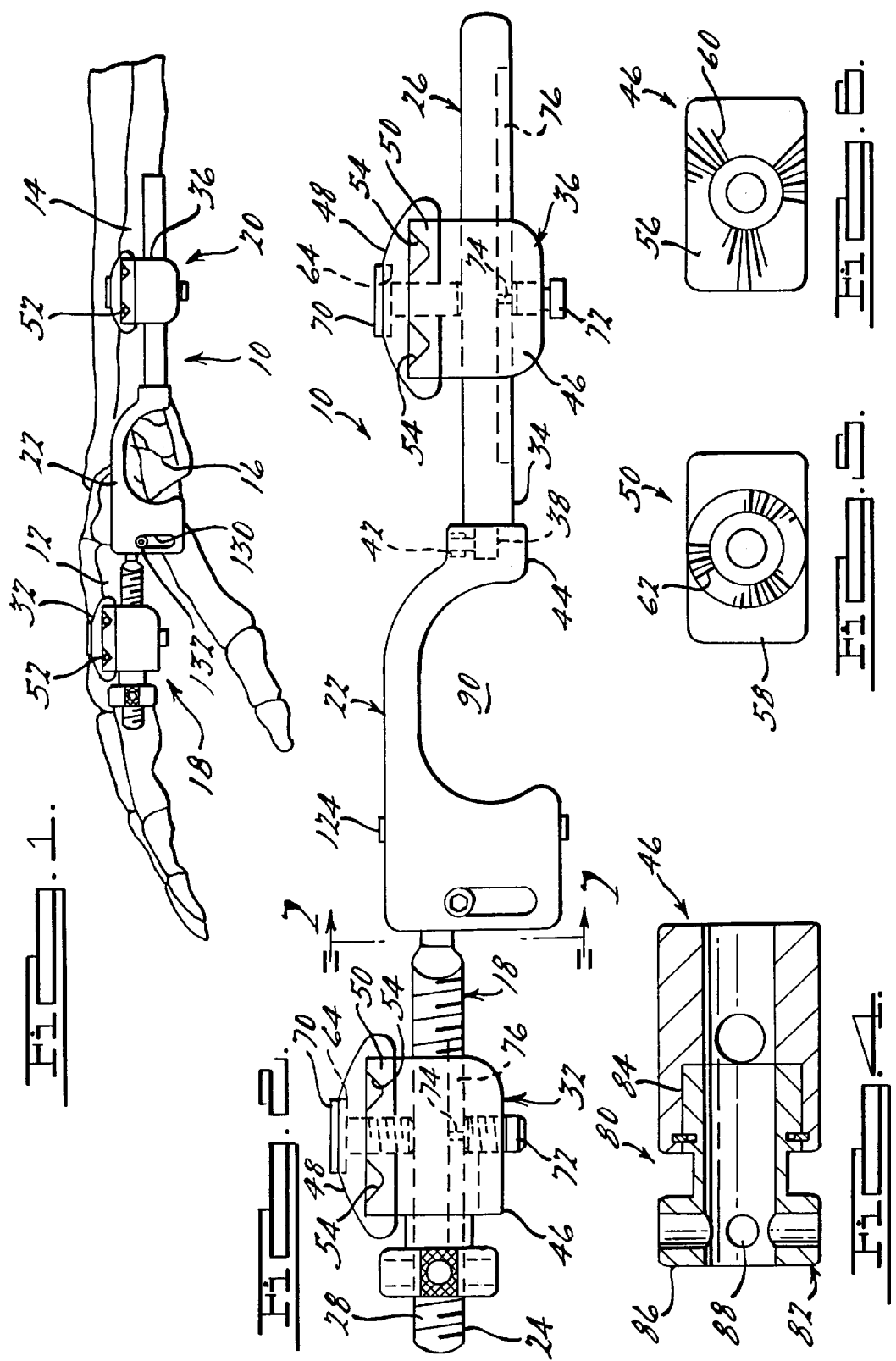

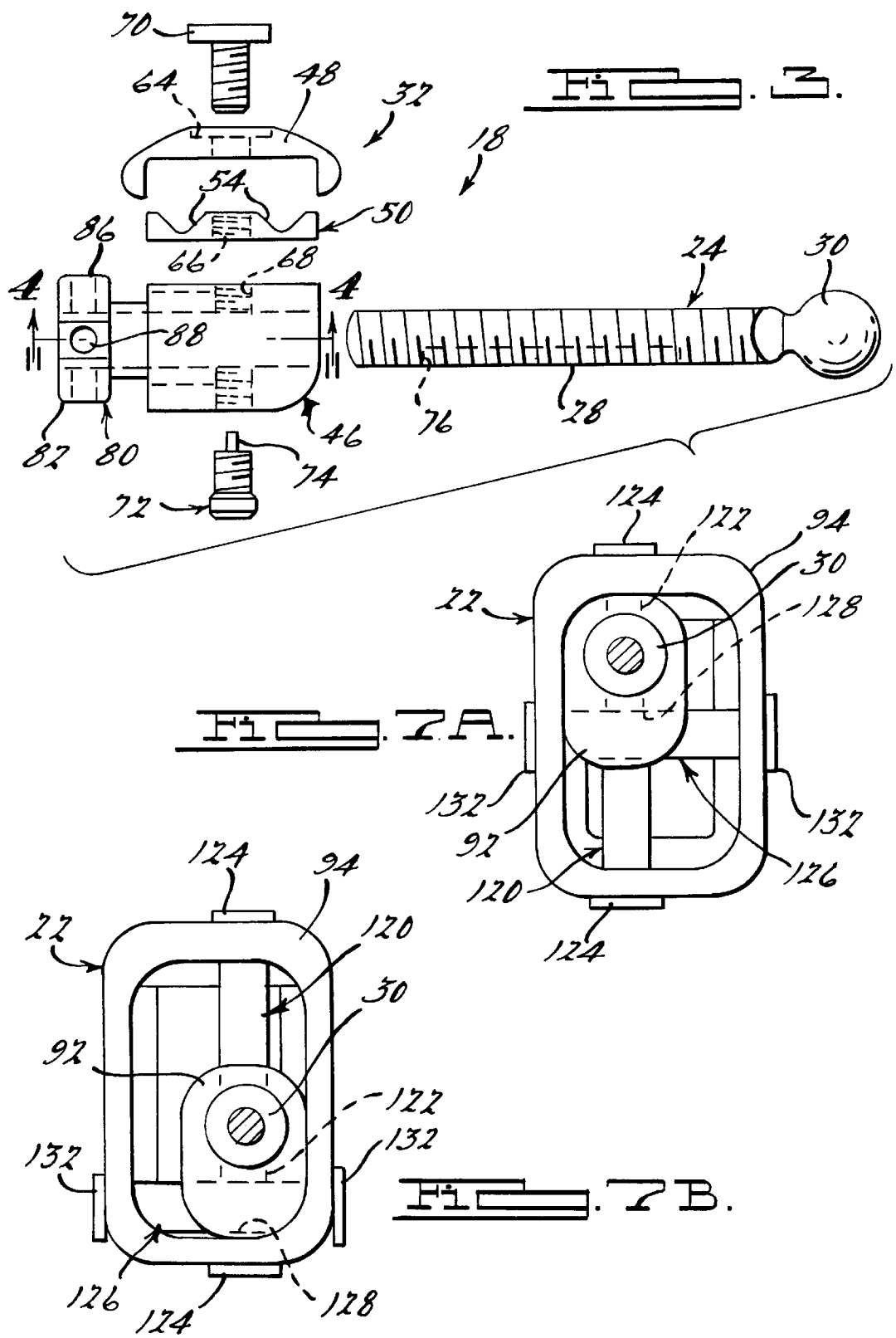

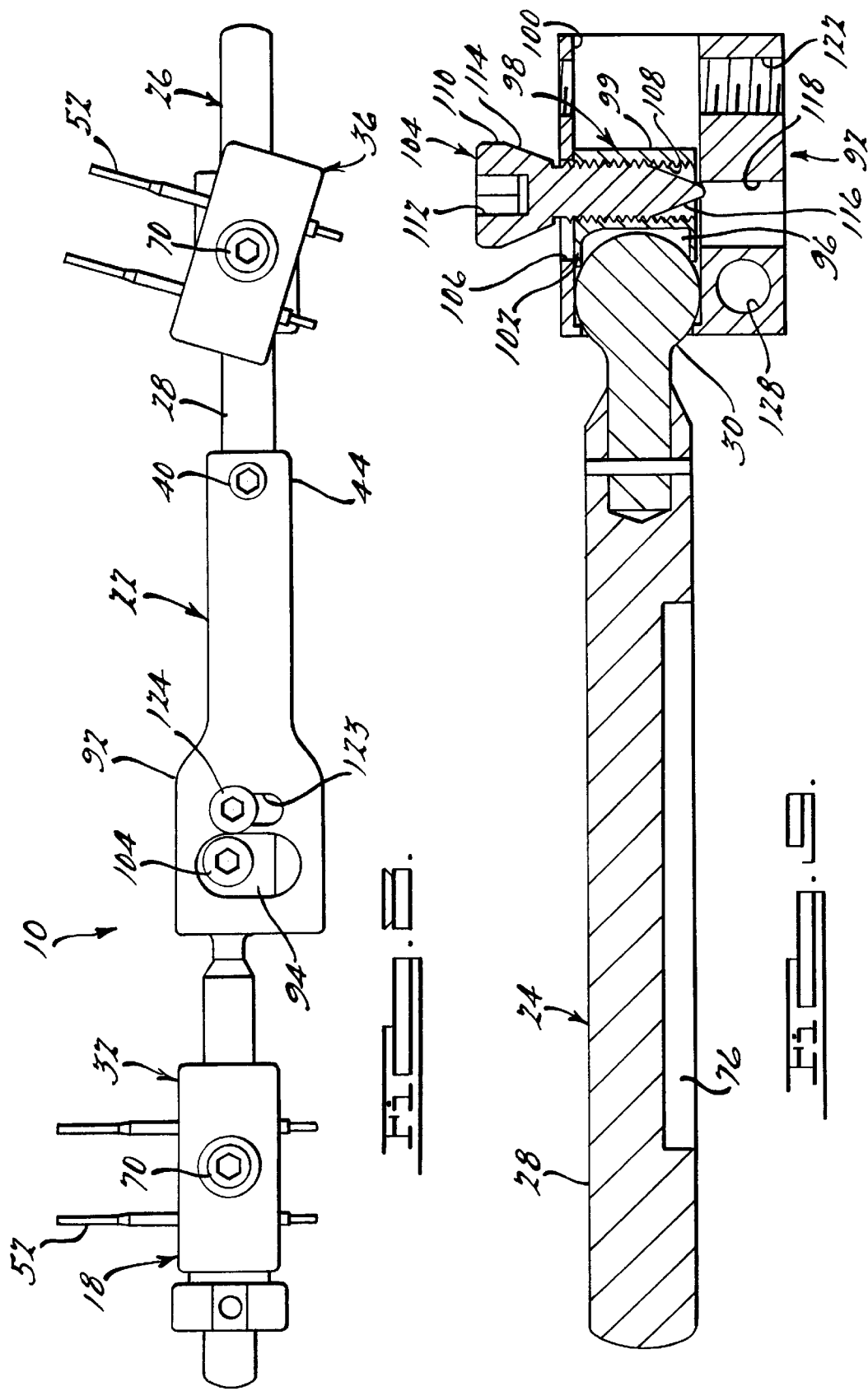

METHOD AND APPARATUS FOR EXTERNAL FIXATION OF SMALL BONES

BACKGROUND OF THE INVENTION

1. Field of the Invention

The present invention relates generally to orthopedic surgical procedures, and more particularly to a method and apparatus for external fixation of small bones.

2. Description of the Related Art

In various orthopedic surgical procedures, it is necessary to secure two or more portions of bone in a relatively fixed relationship to each other. This need is often a result of a fracture which has occurred to the bone. To ensure that the bone can properly regenerate and fuse the fractures of the bone, it is important that the various bone portions be fixed at the desired position during bone regeneration.

Various external fixation devices for the repair of traumatized bone are known. For example, commonly assigned U.S. Pat. No. 5,620,442 to Bailey et al. discloses an apparatus for the external fixation of small bones. The apparatus is illustrated to include a bone screw clamp for receiving a first bone screw which is connected to a first bone portion. The external fixator further includes a bone screw clamp which is operable to receive a second bone screw connected to the second bone portion. The first and second bone screw clamps include a spherical portion. The external fixator further includes a connection member for securing the spherical portions of the bone screw clamps. The connection member defines a radiographic window to permit radiographic examination of the bone fracture without removing the apparatus. U.S. Pat. No. 5,620,442 is hereby incorporated by reference as if fully set forth herein.

While known fixators, including the type described above, have proven to be effective in fixating bones, they nevertheless can be the subject of certain improvements. In this regard, conventional external fixation devices often prohibit the treating physician from performing corrective maneuvers without significantly loosening or disassembling a supportive frame, thereby increasing the risk of fracture misalignment and associated patient discomfort. Thus, it would be advantageous to provide an external fixation device which allows for mechanical adjustment without compromising skeletal fixation and gross mechanical adjustment. It would also be advantageous to provide an external fixation device which allows for gross and mechanical adjustments that are mutually exclusive and independent from one another.

SUMMARY OF THE PRESENT INVENTION

According to one aspect, the present invention relates to a fixator operable for securing two portions of bone in a fixed relationship to each other, with the first bone portion having a first bone screw attached thereto while the second bone portion has a second bone screw attached thereto. The fixator includes a first bone screw clamping assembly for receiving the first bone screw and a second bone screw clamping assembly for receiving the second bone screw. The fixator further includes a connection member interconnecting the first and second bone screw clamping assemblies. The connection member includes a main body portion, means for receiving an end portion of the first bone screw clamping assembly and means for adjusting the end portion relative to the main body portion.

In a preferred form, the end portion of the first bone screw clamping assembly is spherical in shape and the means for receiving the end portion comprises an internal module adjustably mounted within the main body portion of the connection member. The spherical end is adjustably received within the internal module so as to selectively permit universal movement of the spherical end.

To provide means for adjusting the end of the first clamping assembly, the fixator preferably includes first and second rods mounted for rotation relative to the main body portion. The first and second rods are threadably engaged with the internal module such that rotation of the first rod linearly translates the internal module in a first direction and rotation of the second rod linearly translates the internal module in a second direction substantially perpendicular to the first direction.

An advantage of the present invention is to provide a method and apparatus for fixation of small bones that provides both gross and mechanical adjustment without comprising skeletal fixation and gross adjustment.

Another advantage of the present invention is to provide a method and apparatus for fixation of small bones that provides gross and mechanical adjustments which are mutually exclusive and independent of one another.

It is a related advantage of the present invention to provide a method and apparatus for fixation of small bones which permits gross and mechanical adjustments for restoration of radial length through ligamentotaxis, correction of angular deformity and fracture rotation, restoration of volar title, and reparation of radial/ulnar translation.

Another advantage of the present invention is to provide a method and apparatus for fixation of small bones in which the bone screw clamp permits swiveling movement within a plane defined by the associated bone screws, thereby allowing for greater application of more complex fracture patterns requiring screw placement variation.

BRIEF DESCRIPTION OF THE DRAWINGS

FIG. 1 is an illustration of the apparatus for fixation of small bones according to the teachings of the preferred embodiment of the present invention shown in operative association with a wrist joint.

FIG. 2 is an enlarged elevational view of the apparatus for fixation of small bones shown in FIG. 1 according to the teachings of the preferred embodiment of the present invention.

FIG. 3 is a partially exploded view of a portion of the apparatus for fixation of small bones shown in FIG. 1 according to the teachings of the preferred embodiment of the present invention.

FIG. 4 is a cross-sectional view taken along the line 4—4 of FIG. 3.

FIG. 5 is an elevational view of the locking surface formed on the intermediate member of the bone screw clamping assembly shown in FIG. 2.

FIG. 6 is an elevational view of the locking surface formed on the base portion of the bone screw clamping assembly shown in FIG. 2.

FIG. 7(A) is a cross-sectional view taken along the line 7—7 of FIG. 2 illustrating a first operational position of the internal module of the connection member according to the teachings of the preferred embodiment of the present invention.

FIG. 7(B) is a cross-sectional view similar to FIG. 7(A) illustrating a second operational position of the internal module.

FIG. 8 is a top elevational view of the apparatus for fixation of small bones shown in FIG. 1 according to the teachings of the preferred embodiment of the present invention.

FIG. 9 is a cross-sectional view taken through a portion of the apparatus for fixation of small bones shown in FIG. 1 according to the teachings of the preferred embodiment of the present invention illustrating the locking mechanism for arresting universal movement of the spherical portion relative to the connection member.

DETAILED DESCRIPTION OF THE PREFERRED EMBODIMENT

The following description of the preferred embodiment of the present invention is merely exemplary in nature and is in no way intended to limit the subject invention or its application or uses.

Referring to FIG. 1, an apparatus 10 for fixation of small bone portions 12 and 14 is shown constructed in accordance with the teachings of the first preferred embodiment of the present invention. In particular, the apparatus 10 is illustrated as being used to secure a bone fracture 16 which is located in close proximity to the wrist joint. The apparatus 10 is used to secure the bone portions 12 and 14 in a fixed relationship so as to permit the fractured portions to fuse properly. While the apparatus 10 is shown in conjunction with a wrist joint, it will be appreciated that the apparatus 10 may be used with other joints as well.

The construction of the apparatus 10 will now be described with reference to FIGS. 2 through 8. The apparatus 10 is shown to generally include first and second bone screw clamping assemblies 18 and 20 and a central body or connection member 22. The first and second bone screw clamping assemblies 18 and 20 include a first clamp support arm 24 and a second clamp support arm 26, respectively. The first and second clamp support arms 24 and 26 are connected to each other by the connection member 22.

The first clamp support arm 24 includes an extension portion 28 and a spherical portion 30. The extension portion 28 of the first clamp support arm 24 is used to allow a first clamping module 32 to translate thereon as described herein. The spherical projection 30 extends from the extension portion 28 and is used to engage the connection member 22 in a manner described below to permit universal movement between the spherical projection 30 and the connection member 22.

In a similar fashion, the second clamp support arm 26 also includes an extension portion 34. As with the first clamp support arm 24, the extension portion 34 is used to allow a second clamping module 36 to translate thereon. The extension portion 34 includes a generally cylindrical end 38 that is received within a cylindrical recess (not specifically shown) provided in an end 44 of the connection member 22. A set screw 40 extends through an aperture 42 in the connection member 22 and functions to fix the extension portion 34 relative to the connection member 22. Otherwise, the extension portion 34 may be rotated about its longitudinal axis.

While not specifically illustrated, the first and second extension portion 28 and 34 of the first and second clamp support arms 24 and 26 are preferably oval in cross section. In this regard, the extension portions 28 and 34 both include a flat upper surface and a flat lower surface interconnected by a pair of arcuate side portions. The oval cross section of the extension portions 28 and 34 functions to prevent rotation of the first and second bone clamping modules 32 and 36 relative to the first and second extension portions 28 and 34, respectively.

The first bone screw clamping module 32 will be described in greater detail with reference to FIGS. 3–6. It is to be understood that while only the first bone screw clamping module 32 is being described, the second bone screw clamping module 36 will have a similar construction. The first bone screw clamping module 32 is shown to generally include a base portion 46, a cover portion 48, and an intermediate portion 50 therebetween. The intermediate portion 50 serves to receive at least one bone screw 52 in one of a plurality of grooves 54, while the cover portion 48 serves to secure the bone screw 52 within the grooves 54.

As shown most clearly in FIG. 3, the grooves 54 include a pair of contact surfaces which are substantially planar so as to permit line contact of the bone screw 52 in two positions within the grooves 54. Since the bone screw 52 also engages the cover portion 48 of the clamping module 32, the bone screw 52 engages the first bone screw clamping module 32 in three positions (i.e., along the contact surfaces as well as on the cover portion 48). This provides line contact for the bone screw 52 which secures the bone screws 52 in a more effective manner than if the grooves 54 were cylindrical. This is because if the grooves 54 were cylindrical, they would only contact the bone screw 52 in two positions (i.e., one contact surface in the groove 54 and one contact surface on the cover portion 48) since it is generally not possible to have the shape of the groove 54 exactly match the shape of the bone screw 52.

As specifically shown in FIGS. 5 and 6, an upper surface 56 of the base 46 and a lower surface 58 of the intermediate portion 50 are formed to include cooperating locking surfaces 60 and 62, respectively. In the exemplary embodiment illustrated, the upper surface 56 of the base 46 is formed to include a plurality of locking teeth 60 radially extending about a center point. The lower surface 58 of the intermediate portion 50 is formed to include a corresponding plurality of locking teeth 62. The locking teeth 60 and 62 cooperate to permit angular adjustment of the intermediate portion 50 relative to the base portion 46 so as to positively locate the bone screw 52 at one of a plurality of positions in a plane including the bone screw 52 (as shown in the top view of FIG. 8).

The cover portion 48 and intermediate portion 50 include apertures 64 and 66, respectively. The apertures 64 and 66 align with a corresponding aperture 68 formed in the base portion 46 which is internally threaded. The apertures 64 and 66 cooperate to allow a threaded fastener 70 to pass through the cover portion 48 and intermediate portion 50 and into the threaded aperture 68 of the base 46 of the bone screw clamping module 32.

To secure the position of the bone screw clamping modules 32 and 36 on the extension portions 28 and 34 of the first and second clamp support arms 24 and 26, the apparatus 10 of the present invention further includes a plurality of locking screws 72. The locking screws 72 are operable to threadably engage the bases 46 of the bone screw clamping modules 32 and 36 and extend therethrough to engage the extension portions 28 and 34 of the first and second clamp support arms 24 and 26, respectively. In the embodiment shown, each of the locking screws 72 is formed to include a first end 74 having a reduced diameter operable to engage the longitudinal extending channel 76. Accordingly, upon rotation of the locking screws 72, the locking screws 72 are able engage the extension portions 28 and 34 of the first and second clamp support arms 24 and 26 so as to prevent longitudinal movement of the clamping modules 32 and 36.

With reference to FIGS. 3 and 4, the apparatus 10 of the present invention is shown to further include a compression/distraction mechanism 80 for linearly translating the first bone screw clamping module 32 relative to the first clamp support arm 24. The compression/distraction mechanism 80 includes a rotatable sleeve 82 formed to include internal threads in cooperative engagement with external threads formed on the extension portion 28 of the first clamp support arm 24. The rotatable sleeve 82 has a first end 84 rotatably retained within the base 46 of bone screw clamping module 32. The rotatable sleeve 82 further includes an enlarged second end 86 having a partially knurled exterior surface. The exterior surface of the enlarged second end 86 is further formed to include a plurality of radially extending apertures 88 operable for receiving a tool (not shown) for facilitating rotation of the rotatable sleeve 82. Upon selective rotation of the rotatable sleeve 82 relative to the first clamp support arm 24, the first bone screw clamping module 32 is longitudinally displaced relative to the first clamp support arm 24 in a linear direction either toward or away from the spherical projection 30.

In the embodiment illustrated, the second bone screw clamping module 36 is not shown to include a compression/distraction mechanism. In use, after the apparatus 10 is initially attached through the bone screws 52, the second bone screw support clamping module 36 would remain longitudinally fixed relative to the second extension portion 34. Adjustment of the plurality of bone screws 52 held by the second bone screw clamping module 36 relative to the first bone screw clamping module 32 would be accomplished through selective control of the compression/distraction mechanism arranged with the first bone screw clamping module 32. However, it will be appreciated by those skilled in the art that certain applications may alternatively require incorporation of a second compression/distraction mechanism of substantially identical construction.

The connection member 22 will now be described with reference to FIGS. 2, 7A, 7B, 8 and 9. The connection member 22 is generally U-shaped so as to define a radiographic window 90. The radiographic window 90 functions to permit radiographic viewing through the fracture 16 from a lateral direction without removal of the apparatus 10.

To provide means for receiving the spherical projection 30 of the extension portion 24, the connection member 22 includes an internal module 92 disposed within a main body portion 94. The internal module 92, which is shown most clearly in the cross-sectional view of FIG. 9, defines a cavity 96 for receiving the spherical portion 30 and normally permitting universal movement of the spherical portion 30 relative to the internal module 92 and thus relative to the main body 94 of the connection member 22. As will become apparent below, the internal module 92 of the connection member 22 is adjustably interconnected to the main body portion 94.

To provide means for selectively arresting relative rotation of the spherical portion 30, the internal module 92 is shown to include a locking mechanism 98. The locking mechanism 98 includes a clamping member 99 disposed within a horizontally elongated channel 100 of the internal module 92 and includes an open cylindrical end 102 disposed adjacent to the spherical portion 30. A threaded fastener 104 passes through an aperture 106 provided in a top surface of the internal module 92 and threadably engages a vertical aperture 108 in the clamping member 99. The fastener 104 includes a head 110 having a hexagonal recess 112 for receiving a tool for tightening and loosening.

Upon tightening the fastener 104, a tapered surface 114 of the head 110 engages a side of the aperture 106 formed in the top of the internal module 92 and a tapered tip 116 of the fastener 104 engages a side of a lower aperture 118 adapted to receive the fastener 104. Downward advancement of the fastener 104 urges the forward end 102 of the clamping member 99 into engagement with the spherical portion 30, thereby selectively arresting universal movement of the spherical portion 30. While not illustrated, it will be understood that the spherical portion 30 may be provided with a grooved surface to assist in establishing locking engagement with the clamping member 99.

To provide means for linearly translating the spherical portion 30 relative to the main body 94 of the connection member 22, the apparatus 10 of the present invention preferably includes means for linearly translating the spherical member 30 in a first direction relative to the main body portion 94 and means for linearly translating the spherical member 30 in a second direction, which is substantially perpendicular to the first direction, relative to the main body portion 94.

The means for translating the spherical portion 30 in a first direction is shown to preferably comprise a threaded rod 120 which passes through an internally threaded aperture 122 vertically extending through the internal module 92. The threaded rod 120 extends through apertures 123 provided in an upper surface and a lower surface of the frame of the connection member 22. Each end of the threaded rod 120 is provided with a head 124 having a hexagonal recess. Rotation of the threaded rod 120 selectively translates the internal module 92 in one of an upward and a downward direction (as viewed from a lateral direction) so as to mechanically adjust volar tilt.

In a similar manner, the means for linearly translating the internal module 92 in a second direction is shown to preferably comprise a threaded rod 126 laterally (e.g., horizontally) extending through an internally threaded aperture 128 provided in the internal module 92. Again, the threaded rod 126 passes through apertures 130 provided in opposite sides of the frame and terminates in a pair of heads 132 each provided with a hexagonal recess. Selective rotation of the threaded rod 126 causes linear translation of the internal module 92 and thereby the spherical portion 30 in opposing lateral directions so as to provide a mechanical radial/ulnar adjustment. The ranges of adjustably of the internal module 92 through selective rotation of the threaded rods 120 and 126 is illustrated in FIGS. 7A and 7B.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for securing a first bone portion in a fixed relationship to a second bone portion by a first bone screw connected to the first bone portion, and a second bone screw connected to the second bone portion, the apparatus comprising:

a first bone screw clamping assembly for receiving the first bone screw, said first bone screw clamping assembly having an elongated support arm defining an elongate axis and having an end;

a second bone screw clamping assembly for receiving said second bone screw; and a connection member interconnecting said first and second bone screw clamping assemblies, said connection member including a main body portion, means for receiving said end, and means for linearly adjusting said end relative to said main body portion, said means for linearly adjusting being gear driven;

wherein said means for linearly adjusting said end relative to said main body portion is operative for linearly translating said end relative to said main body portion in a direction perpendicular to said first bone screw and perpendicular to said elongate axis.

2. The apparatus for securing a first bone portion in a fixed relationship to a second bone portion of claim 1, wherein said means for linearly adjusting said end relative to said main body portion is operable for linearly translating said end in first and second directions relative to said main body portion, said second direction being substantially perpendicular to said first direction.

3. The apparatus for securing a first bone portion in a fixed relationship to a second bone portion of claim 2, wherein said end is independently translatable in both of said first and second directions.

4. The apparatus for securing a first bone portion in a fixed relationship to a second bone portion of claim 1, wherein said means for receiving said end selectively permits universal movement of said end relative to said connection member.

5. The apparatus for securing a first bone portion in a fixed relationship to a second bone portion of claim 4, wherein said connection member includes locking means for preventing universal movement of said end relative to said connection member.

6. The apparatus for securing a first bone portion in a fixed relationship to a second bone portion of claim 1, wherein means for linearly adjusting said end relative to said main body portion comprises an internal module disposed within said main body portion and a threaded shaft interconnecting said main body portion and said internal module.

7. An apparatus for securing a first bone portion in a fixed relationship to a second bone portion by a first bone screw connected to the first bone portion and a second bone screw connected to the second bone portion, the apparatus comprising:

a first clamping assembly for receiving the first bone screw, said first clamping assembly including an elongated arm defining an elongate axis and having an end;

a second clamping assembly for receiving the second bone screw; and a connection member for interconnecting said first and second clamping assemblies, said connection member including a main body and a module mounted to said main body for linear movement relative to said main body, said module receiving said end to allow pivoting of said first clamping assembly about said end;

wherein said module is linearly translatable relative to said main body of said connection member in a direction perpendicular to said first bone screw and perpendicular to said elongate axis.

8. The apparatus for securing a first bone portion in a fixed relationship to a second bone portion of claim 7, wherein said module is linearly translatable in first and second directions relative to said main body of said connection member, said second direction being substantially perpendicular to said first direction.

9. The apparatus for securing a first bone portion in a fixed relationship to a second bone portion of claim 8, wherein said module is independently translatable in both of said first and second directions.

10. The apparatus for securing a first bone portion in a fixed relationship to a second bone portion of claim 7, wherein universal movement is selectively permitted between said module and said end.

11. The apparatus for securing a first bone portion in a fixed relationship to a second bone portion of claim 10, further including a locking mechanism for preventing universal movement of said end.

12. The apparatus for securing a first bone portion in a fixed relationship to a second bone portion of claim 7, wherein said module is interconnected to said main body portion through a first threaded shaft such that rotation of said first threaded shaft linearly translates said module in said first direction.

13. The apparatus for securing a first bone portion in a fixed relationship to a second bone portion of claim 12, wherein said module is further interconnected to said main body portion through a second threaded shaft such that rotation of said second threaded shaft linearly translates said module in a second direction substantially perpendicular to said first direction.

14. An apparatus for securing a first bone portion in a fixed relationship to a second bone portion by a first bone screw connected to the first bone portion and a second bone screw connected to the second bone portion, the apparatus comprising:

a first clamping assembly for receiving the first bone screw, said first clamping assembly including a spherical portion;

a second clamping assembly for receiving the second bone screw; and a connection member for interconnecting said first and second clamping assemblies, said connection member including a main body portion and a module mounted to said main body portion for linear movement relative to said main body portion, said module receiving said spherical portion so as to permit universal movement thereof.

15. The apparatus for securing a first bone portion in a fixed relationship to a second bone portion of claim 14, further comprising a first rod mounted for rotation relative to said main body portion and threadably engaged with said module such that rotation of said first rod linearly translates said module in a first direction.

16. The apparatus for securing a first bone portion in a fixed relationship to a second bone portion of claim 15, further comprising a second rod mounted for rotation relative to said main body portion and threadably engaged with said module such that rotation of said second rod linearly translates said module in a first direction, said first direction being substantially perpendicular to said second direction.

17. The apparatus for securing a first bone portion in a fixed relationship to a second bone portion of claim 14, further comprising a locking mechanism for selectively preventing universal movement of said spherical portion.

18. The apparatus for securing a first bone portion in a fixed relationship to a second bone portion of claim 14, wherein said main body portion at least partially defines a radiographic window for permitting radiographic examination of the fixed relationship of the first bone portion and the second bone portion from a lateral direction.

* * * * *

UNITED STATES PATENT AND TRADEMARK OFFICE
CERTIFICATE OF CORRECTION

PATENT NO. : 6,010,501  Page 1 of 1
DATED : January 4, 2000
INVENTOR(S) : Keith B. Raskin, Stephen B. Walulik, Kirk J. Bailey It is certified that error appears in the above-identified patent and that said Letters Patent is hereby corrected as shown below:

Column 3,
Line 57, "portion" should be -- portions --

Column 4,
Line 62, after "able" insert -- to --

Column 6,
Line 43, "adjustably" should be -- adjustability --

Signed and Sealed this

Twenty-sixth Day of February, 2002

Attest:

JAMES E. ROGAN
*Attesting Officer*  *Director of the United States Patent and Trademark Office*